United States Patent
Whalley et al.

(10) Patent No.: US 11,419,829 B2
(45) Date of Patent: Aug. 23, 2022

(54) USE OF CANNABIDIOL IN COMBINATION WITH 5-HT2B RECEPTOR AGONISTS OR AMPHETAMINES IN THE TREATMENT OF EPILEPSY

(71) Applicant: GW Research Limited, Cambridge (GB)

(72) Inventors: Benjamin Whalley, Cambridge (GB); Geoffrey Guy, Cambridge (GB); Volker Knappertz, Cambridge (GB); Royston Gray, Cambridge (GB); Rohini Rana, Cambridge (GB)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 16/651,751

(22) PCT Filed: Oct. 1, 2018

(86) PCT No.: PCT/GB2018/052805
§ 371 (c)(1),
(2) Date: Mar. 27, 2020

(87) PCT Pub. No.: WO2019/064031
PCT Pub. Date: Apr. 4, 2019

(65) Prior Publication Data
US 2020/0237683 A1 Jul. 30, 2020

(30) Foreign Application Priority Data

Sep. 29, 2017 (GB) ...................................... 1715919
Apr. 20, 2018 (GB) ...................................... 1806481

(51) Int. Cl.
*A61K 31/05* (2006.01)
*A61K 31/137* (2006.01)
*A61P 25/08* (2006.01)

(52) U.S. Cl.
CPC ............ *A61K 31/05* (2013.01); *A61K 31/137* (2013.01); *A61P 25/08* (2018.01)

(58) Field of Classification Search
CPC ................ A61K 31/137; A61K 31/165; A61K 31/352; A61K 31/05; A61P 25/08
See application file for complete search history.

(56) References Cited

U.S. PATENT DOCUMENTS

| | | | |
|---|---|---|---|
| 5,952,388 A * | 9/1999 | Loscher | A61P 25/08 514/654 |
| 2015/0359756 A1 | 6/2015 | Guy et al. | |
| 2017/0239193 A1 | 4/2017 | Guy et al. | |
| 2018/0228751 A1 | 2/2018 | Stott et al. | |
| 2018/0071210 A1 | 3/2018 | Wilkhu et al. | |
| 2019/0167583 A1 | 6/2019 | Shah | |
| 2019/0175547 A1 | 6/2019 | Nabissi | |
| 2019/0321307 A1 | 6/2019 | Wright et al. | |
| 2019/0365667 A1 | 8/2019 | Wilkhu | |
| 2019/0314296 A1 | 10/2019 | Wright et al. | |
| 2020/0138738 A1 | 1/2020 | Guy et al. | |
| 2020/0179303 A1 | 2/2020 | Guy et al. | |
| 2020/0237683 A1 | 3/2020 | Whalley et al. | |
| 2020/0297656 A1 | 6/2020 | Guy et al. | |
| 2020/0206152 A1 | 7/2020 | Jones et al. | |

(Continued)

FOREIGN PATENT DOCUMENTS

| | | |
|---|---|---|
| GB | 2531282 A | 4/2016 |
| GB | 2539472 A | 12/2016 |

(Continued)

OTHER PUBLICATIONS

Kelley et al., Develop. Med. & Child Neur., vol. 52, pp. 988-993, publ. 2010 (Year: 2010).*
Ceulemans, B. et al., "Successful use of fenfluramine as an add-on treatment for Dravet syndrome," Epilepsia, 53(7):1131-1139 (2012).
Dravet, C., "The core Dravet syndrome phenotype," Epilepsia. 52 Suppl 2:3-9. doi: 10.1111/j.1528-1167.2011.02994.x. (2011).
Eadie, M. J., "Shortcomings in the current treatment of epilepsy," Expert Rev Neurother, 12(12):1419-27 (2012).
Rothman, R. B. & Baumann, M. H., "Serotonergic Drugsand Valvular Heart Disease," Expert Opin Drug Saf., 8(3):317-329 (2009), 21 pages; doi:10.1517/14740330902931524.

(Continued)

*Primary Examiner* — Sarah Pihonak
(74) *Attorney, Agent, or Firm* — Cooley LLP

(57) ABSTRACT

The present invention relates to the use of cannabidiol (CBD) in combination with an agonist of 5-HT2B receptors. Such a combination provides protection against the adverse effects caused by agonists of 5-HT2B receptors. The invention further relates to the use of CBD in combination5 with an amphetamine or amphetamine derivative in the treatment of epilepsy. In one embodiment the CBD is used in combination with the amphetamine derivative fenfluramine to produce a significant reduction in seizures. Preferably the CBD used is in the form of a highly purified extract of cannabis such that the CBD is present at greater than 98% of the total extract (w/w) and the other components of the extract are characterised. In particular the cannabinoid10 tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD. In use the CBD in combination with an agonist of 5-HT2B receptors, amphetamine or amphetamine derivative may be formulated for administration separately, sequentially or simultaneously with the15 amphetamine or amphetamine derivative or the combination may be provided in a single dosage form. Where the CBD is formulated for administration separately, sequentially or simultaneously it may be provided as a kit or together with instructions to administer the one or more components in the manner indicated.

17 Claims, 5 Drawing Sheets

(56) References Cited

U.S. PATENT DOCUMENTS

| | | |
|---|---|---|
| 2020/0206153 A1 | 7/2020 | Whalley et al. |
| 2020/0352878 A1 | 7/2020 | Guy et al. |
| 2020/0368179 A1 | 8/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0093581 A1 | 4/2021 | Guy et al. |

FOREIGN PATENT DOCUMENTS

| | | | |
|---|---|---|---|
| WO | WO 2014/177676 A1 | 11/2014 | |
| WO | WO-2015193668 A1 * | 12/2015 | ........... A61K 36/185 |
| WO | WO 2017/035267 A1 | 3/2017 | |
| WO | WO 2018/037306 A1 | 3/2018 | |
| WO | WO 2018/206924 A1 | 11/2018 | |

OTHER PUBLICATIONS

Schoonjans, A-S. et al., "Cardiovascular safety of low-dose fenfluramine in Dravet syndrome: a review of its benefit-risk profile in a new patient population," Current Medical Research and Opinion, 33:10:1773-1781 (2017).

Thurman, D. J. et al., "Standards for epidemiologic studies and surveillance of epilepsy," Epilepsia, 52 (Suppl 7):2-26 (2011).

Sourbron, J. et al., "Serotonergic Modulation as Effective Treatment for Dravet Syndrome in a Zebrafish Mutant Model," ACS Chem. Neurosci. 7:588-598 (2016).

Kwan, P., "Definition of drug resistant epilepsy: consensus proposal by the ad hoc Task Force of the ILAE Commission on Therapeutic Strategies," Epilepsia, 51(6):1069-1077 (2010).

Mudigoudar, B. et al., "Emerging Antiepileptic Drugs for Severe Pediatric Epilepsies," Semin Pediatr Neurol, 23:167-179 (2016).

Devinsky, O. et al., "Trial of Cannabidiol for Drug-Resistant Seizures in the Dravet Syndrome," N Engl J Med, 376:2011-2020 (2017).

* cited by examiner

Effect of CBD and 7-OH-CBD at the human recombinant 5-HT$_{2B}$ receptor

USE OF CANNABIDIOL IN COMBINATION WITH 5-HT2B RECEPTOR AGONISTS OR AMPHETAMINES IN THE TREATMENT OF EPILEPSY

CROSS-REFERENCE

This application claims the benefit of International PCT Application No. PCT/GB2018/052805, filed Oct. 1, 2018; Great Britain Application No. 1806481.6, filed Apr. 20, 2018; and Great Britain Application No. 1715919.5, filed Sep. 29, 2017; all of which are incorporated herein by reference in their entirety.

FIELD OF THE INVENTION

The present invention relates to the use of cannabidiol (CBD) in combination with an agonist of $5\text{-HT}_{2B}$ receptors. Such a combination provides protection against the adverse effects caused by agonists of $5\text{-HT}_{2B}$ receptors. The invention further relates to the use of CBD in combination with an amphetamine or amphetamine derivative in the treatment of epilepsy. In one embodiment the CBD is used in combination with the amphetamine derivative and $5\text{-HT}_{2B}$ receptor agonist fenfluramine to produce a significant reduction in seizures.

Preferably the CBD used is in the form of a highly purified extract of cannabis such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

In use the CBD in combination with the agonist of $5\text{-HT}_{2B}$ receptors, amphetamine or amphetamine derivative may be formulated for administration separately, sequentially or simultaneously with the amphetamine or amphetamine derivative or the combination may be provided in a single dosage form. Where the CBD is formulated for administration separately, sequentially or simultaneously it may be provided as a kit or together with instructions to administer the one or more components in the manner indicated.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from, an investigation into the type of seizures that the patient is experiencing is undertaken. Clinical observations and electroencephalography (EEG) tests are conducted and the type(s) of seizures are classified according to the ILAE classification described below.

The International classification of seizure types proposed by the ILAE was adopted in 1981 and a revised proposal was published by the ILAE in 2010 and has not yet superseded the 1981 classification. FIG. 1 is adapted from the 2010 proposal for revised terminology and includes the proposed changes to replace the terminology of partial with focal. In addition, the term "simple partial seizure" has been replaced by the term "focal seizure where awareness/responsiveness is not impaired" and the term "complex partial seizure" has been replaced by the term "focal seizure where awareness/consciousness is impaired".

Generalised seizures, where the seizure arises within and rapidly engages bilaterally distributed networks, can be split into six subtypes: Tonic-Clonic (grand mal) seizures; Absence (petit mal) Seizures; Clonic Seizures; Tonic Seizures; Atonic Seizures and Myoclonic Seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a Bilateral convulsive seizure, which is the proposed terminology to replace Secondary Generalised Seizures (generalized seizures that have evolved from focal seizures and are no longer remain localized).

Epileptic syndromes often present with many different types of seizure and identifying the types of seizure that a patient is suffering from is important as many of the standard AED's are targeted to treat or are only effective against a given seizure type/sub-type.

One such childhood epilepsy is Dravet syndrome. Onset of Dravet syndrome almost always occurs during the first year of life with clonic and tonic-clonic seizures in previously healthy and developmentally normal infants (Dravet, 2011). Symptoms peak at about five months of age. Other seizures develop between one and four years of age such as prolonged focal dyscognitive seizures and brief absence seizures.

In diagnosing Dravet syndrome both focal and generalised seizures are considered to be mandatory, Dravet patients may also experience atypical absence seizures, myoclonic absence seizures, atonic seizures and non-convulsive status epilepticus.

Seizures progress to be frequent and treatment-resistant, meaning that the seizures do not respond well to treatment. They also tend to be prolonged, lasting more than 5 minutes. Prolonged seizures may lead to status epilepticus, which is a seizure that lasts more than 30 minutes, or seizures that occur in clusters, one after another.

Prognosis is poor and approximately 14% of children die during a seizure, because of infection, or suddenly due to uncertain causes, often because of the relentless neurological decline. Patients develop intellectual disability and lifelong ongoing seizures. Intellectual impairment varies from severe in 50% patients, to moderate and mild intellectual disability each accounting for 25% of cases.

There are currently no FDA approved treatments specifically indicated for Dravet syndrome. The standard of care usually involves a combination of the following anticonvulsants: clobazam, clonazepam, levetiracetam, topiramate and valproic acid.

Stiripentol is approved in Europe for the treatment of Dravet syndrome in conjunction with clobazam and valproic acid. In the US, stiripentol was granted an Orphan Designation for the treatment of Dravet syndrome in 2008; however, the drug is not FDA approved.

Potent sodium channel blockers used to treat epilepsy actually increase seizure frequency in patients with Dravet Syndrome. The most common are phenytoin, carbamazepine, lamotrigine and rufinamide.

Management may also include a ketogenic diet, and physical and vagus nerve stimulation. In addition to anticonvulsive drugs, many patients with Dravet syndrome are treated with anti-psychotic drugs, stimulants, and drugs to treat insomnia.

Common AED defined by their mechanisms of action are described in the following tables:

TABLE 1

Examples of narrow spectrum AED

| Narrow-spectrum AED | Mechanism | Indication |
|---|---|---|
| Phenytoin | Sodium channel | Complex partial<br>Tonic-clonic |
| Phenobarbital | GABA/Calcium channel | Partial seizures<br>Tonic-clonic |
| Carbamazepine | Sodium channel | Partial seizures<br>Tonic-clonic<br>Mixed seizures |
| Oxcarbazepine | Sodium channel | Partial seizures<br>Tonic-clonic<br>Mixed seizures |
| Gabapentin | Calcium channel | Partial seizures<br>Mixed seizures |
| Pregabalin | Calcium channel | Adjunct therapy for partial seizures with or without secondary generalisation |
| Lacosamide | Sodium channel | Adjunct therapy for partial seizures |
| Vigabatrin | GABA | Secondarily generalized tonic-clonic seizures<br>Partial seizures<br>Infantile spasms due to West syndrome |

TABLE 2

Examples of broad spectrum AED

| Broad-spectrum AED | Mechanism | Indication |
|---|---|---|
| Valproic acid | GABA/Sodium channel | First-line treatment for tonic-clonic seizures, absence seizures and myoclonic seizures<br>Second-line treatment for partial seizures and infantile spasms.<br>Intravenous use in status epilepticus |
| Lamotrigine | Sodium channel | Partial seizures<br>Tonic-clonic<br>Seizures associated with Lennox-Gastaut syndrome |
| Ethosuximide | Calcium channel | Absence seizures |
| Topiramate | GABA/Sodium channel | Seizures associated with Lennox-Gastaut syndrome |
| Zonisamide | GABA/Calcium/Sodium channel | Adjunctive therapy in adults with partial-onset seizures<br>Infantile spasm<br>Mixed seizure<br>Lennox-Gastaut syndrome<br>Myoclonic<br>Generalised tonic-clonic seizure |
| Levetiracetam | Calcium channel | Partial seizures<br>Adjunctive therapy for partial, myoclonic and tonic-clonic seizures |
| Clonazepam | GABA | Typical and atypical absences<br>Infantile myoclonic<br>Myoclonic seizures<br>Akinetic seizures |
| Rufinamide | Sodium channel | Adjunctive treatment of partial seizures associated with Lennox-Gastaut syndrome |

TABLE 3

Examples of AED used specifically in childhood epilepsy

| AED | Mechanism | Indication |
|---|---|---|
| Clobazam | GABA | Adjunctive therapy in complex partial seizures<br>Status epilepticus<br>Myoclonic<br>Myoclonic-absent<br>Simple partial<br>Complex partial<br>Absence seizures<br>Lennox-Gastaut syndrome |
| Stiripentol | GABA | Severe myoclonic epilepsy in infancy (Dravet syndrome) |

The 5-HT$_2$ receptor, also known as the serotonin receptor, has three different sub-types, the 5-HT$_{2A}$ receptor, the 5-HT$_{2B}$ receptor and the 5-HT$_{2C}$ receptor. Some compounds have affinity for all three sub-types of receptor, others only for one or two of the sub-types. These receptors are stimulated by monoamine neurotransmitters which include serotonin, dopamine and norepinephrine. Agonists of the 5-HT$_2$ receptor are common targets for pharmaceutical drugs as agonism of the 5-HT$_2$ receptor has been shown to therapeutically benefit many conditions including obesity, psychiatric disorders, sexual dysfunction and urinary incontinence.

However, activation of these receptors is associated with serious and potentially life threatening adverse effects. Activation of $5\text{-}HT_{2A}$ receptors can induce hallucinations, and the activation of $5\text{-}HT_{2B}$ receptors has been implicated in valvular heart disease and pulmonary hypertension.

There are many known agonists of the $5\text{-}HT_2$ receptor, some of which have been developed as pharmaceutical medications. Agomelatine which has therapeutic use as an anti-depressant, this compound is an agonist of the $5\text{-}HT_{2C}$ receptor. Guanfacine, a sympatholytic drug used to treat hypertension and attention deficit hyperactivity disorder (ADHD) is an agonist of the $5\text{-}HT_{2B}$ receptor. Pergolide, an ergoline-based dopamine receptor agonist used the treatment of Parkinson's disease has agonist properties at the $5\text{-}HT_{2B}$ receptor. Fenfluramine and norfenfluramine are amphetamine derivatives which are potent agonists of the $5\text{-}HT_{2A}$, $5\text{-}HT_{2B}$, and $5\text{-}HT_{2C}$ receptors.

The amphetamine derivative fenfluramine was approved as an anorectic used to treat obesity in 1973. The drug was withdrawn in 1997 after adverse reports of heart valve disease and pulmonary hypotension affecting 12% of men and 20% of women using the drug. The mechanism of action for fenfluramine is to produce the release of serotonin by disrupting vesicular storage of the neurotransmitter and reversing serotonin transporter function resulting in a feeling of fullness and a reduced appetite.

A low dose of between 0.25 and 1.0 mg/kg/day of fenfluramine has been shown to reduce seizure frequency in patients with Dravet syndrome (Schoonjans et al. 2017).

There is currently no approved therapeutic use of the drug fenfluramine.

Amphetamines and amphetamine derivatives includes all derivative compounds which are formed by replacing, or substituting, one or more hydrogen atoms in the amphetamine core structure with substituents. The compounds in this class span a variety of pharmacological subclasses, including stimulants, empathogens, and hallucinogens. Examples of amphetamine derivatives are amphetamine, methamphetamine, ephedrine, cathinone, phentermine, mephentermine, bupropion, methoxyphenamine, selegiline, amfepramone, fenfluramine, pyrovalerone, MDMA (ecstasy), and DOM (STP).

It has been found that CBD and its human metabolite 7-hydroxy cannabidiol (7-OH CBD) are antagonists at the $5\text{-}HT_{2B}$ receptor. Surprisingly, the use of CBD can protect against the adverse effects associated with the use of $5\text{-}HT_{2B}$ agonists whilst retaining the therapeutic effects of the agonist. Such therapeutic effects of $5\text{-}HT_{2B}$ receptor agonists such as fenfluramine and norfenfluramine include appetite suppression and reduction of seizures in epilepsy.

The applicant has shown that the co-administration of CBD with an agonist of the $5\text{-}HT_{2B}$ receptor, such as fenfluramine, would reduce or prevent the valvular heart disease risk that is associated with agonism of the $5\text{-}HT_{2B}$ receptors. This is due to the ability of CBD to block the $5\text{-}HT_{2B}$ receptors preventing agonists such as fenfluramine from activating the receptors.

Furthermore, co-administration of CBD with pharmaceutical agents such as fenfluramine would not adversely affect its beneficial effects on therapeutic targets such as seizures as we show that CBD does not act upon the $5\text{-}HT_{2C}$ receptors through which fenfluramine is proposed to exert its effects on seizures.

In addition, the applicant has demonstrated that the co-administration of CBD with an amphetamine or amphetamine derivative such as fenfluramine produces a synergistic reduction in seizures in an animal model of epilepsy.

BRIEF SUMMARY OF THE DISCLOSURE

In accordance with a first aspect of the present invention there is provided cannabidiol (CBD) in combination with a $5\text{-}HT_{2B}$ receptor agonist, an amphetamine or an amphetamine derivative for use in the treatment of epilepsy.

Preferably the combination is for use in the prevention or reduction of side effects associated with agonism of the $5\text{-}HT_{2B}$ receptor.

Preferably the $5\text{-}HT_{2B}$ receptor agonist, amphetamine or amphetamine derivative is one or more of: guanfacine; 3,4-Methylenedioxymethamphetamine (MDMA); Methylenedioxyamphetamine (MDA); 2,5-Dimethoxy-4-ethoxyamphetamine (MEM); pergolide; cabergoline; norfenfluramine; fenfluramine; chlorphentermine; aminorex; meta-chlorophenylpiperazine (mCPP); bromo-dragonfly; N,N-Dimethyltryptamine (DMT); 5-methoxy-N,N-dimethyltryptamine (5-MeO-DMT); lysergic acid diethylamide (LSD-25); psilocin; amphetamine; methamphetamine; ephedrine; cathinone; phentermine; mephentermine; bupropion; methoxyphenamine; selegiline; amfepramone; n-fenfluramine; pyrovalerone; MDMA (ecstasy) and DOM (STP).

More preferably the $5\text{-}HT_{2B}$ receptor agonist, amphetamine or amphetamine derivative is norfenfluramine or fenfluramine.

Preferably the side effects that are prevented or reduced is heart valve disease.

In one embodiment the CBD is in the form of a highly purified extract of *cannabis* which comprises at least 98% (w/w) CBD. Preferably the highly purified extract comprises less than 0.15% THC and up to 1% CBDV.

In a separate embodiment the CBD is present as a synthetic compound.

Preferably the epilepsy is treatment resistant epilepsy (TRE). More preferably the TRE is one of: Dravet Syndrome; Myoclonic-Absence Epilepsy; Lennox-Gastaut syndrome; Generalized Epilepsy of unknown origin; CDKL5 mutation; Aicardi syndrome; tuberous sclerosis complex; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome.

Preferably the ratio of CBD to $5\text{-}HT_{2B}$ receptor agonist, amphetamine or amphetamine derivative is between 20:1 to 1:20, more preferably 10:1 to 1:10, more preferably still 3:1 to 1:3, to 2:1 to 1:2, more preferably still the ratio is approximately 1:1.

Preferably the dose of CBD is between 5 and 50 mg/kg/day and the dose of a $5\text{-}HT_{2B}$ receptor agonist, amphetamine or amphetamine derivative is below 0.01 and 1 mg/kg/day.

In accordance with a second aspect of the present invention there is provided a method of treating epilepsy comprising administering cannabidiol (CBD) in combination with a $5\text{-}HT_{2B}$ receptor agonist, an amphetamine or an amphetamine derivative to a subject. Preferably the subject is a human.

BRIEF DESCRIPTION OF THE DRAWINGS

Embodiments of the invention are further described hereinafter with reference to the accompanying drawings, in which.

DEFINITIONS

Figure 1:
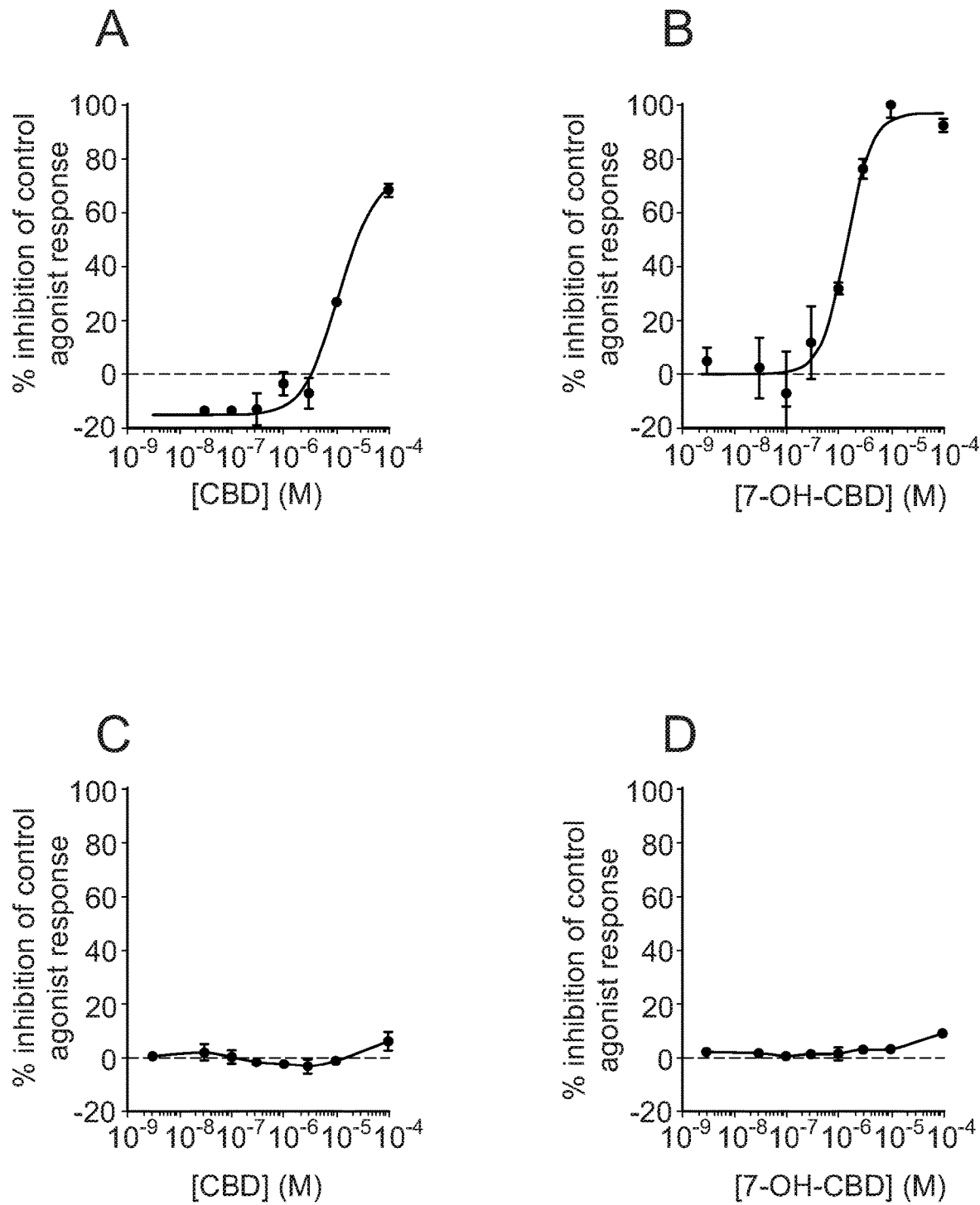
FIG. 1 shows the effect of CBD and 7-OH-CBD at the human recombinant $5\text{-}HT_{2B}$ receptor.

Definitions of some of the terms used to describe the invention are detailed below:

The cannabinoids described in the present application are listed below along with their standard abbreviations.

TABLE 4

Cannabinoids and their abbreviations

| Abbreviation | Name |
|---|---|
| CBD | Cannabidiol |
| CBDA | Cannabidiolic acid |
| CBDV | Cannabidivarin |
| CBDVA | Cannabidivarinic acid |
| THC | Tetrahydrocannabinol |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoid extracts" are defined as cannabinoids that have been extracted from the cannabis plant and purified to the extent that other cannabinoids and non-cannabinoid components that are co-extracted with the cannabinoids have been substantially removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example, it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Childhood epilepsy" refers to the many different syndromes and genetic mutations that can occur to cause epilepsy in childhood. Examples of some of these are as follows: Dravet Syndrome; Myoclonic-Absence Epilepsy; Lennox-Gastaut syndrome; Generalized Epilepsy of unknown origin; CDKL5 mutation; Aicardi syndrome; tuberous sclerosis complex; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

The term "5-HT$_{2B}$ receptor agonist" refers to any compound, with or without pharmaceutical or therapeutic use. Examples of such compounds includes but is not limited to: guanfacine; 3,4-Methylenedioxymethamphetamine (MDMA); Methylenedioxyamphetamine (MDA); 2,5-Dimethoxy-4-ethoxyamphetamine (MEM); pergolide; cabergoline; norfenfluramine; fenfluramine; chlorphentermine; aminorex; meta-chlorophenylpiperazine (mCPP); bromodragonfly; N,N-Dimethyltryptamine (DMT); 5-methoxy-N,N-dimethyltryptamine (5-MeO-DMT); lysergic acid diethylamide (LSD-25); and psilocin.

The term "amphetamine" or "amphetamine derivative" refers to compounds that of the class amphetamine or are formed by replacing, or substituting, one or more hydrogen atoms in the amphetamine core structure with substituents. The compounds in this class span a variety of pharmacological subclasses, including stimulants, empathogens, and hallucinogens. Examples of these include amphetamine; methamphetamine; ephedrine; cathinone; phentermine; mephentermine; bupropion; methoxyphenamine; selegiline; amfepramone; fenfluramine, n-fenfluramine; pyrovalerone; MDMA (ecstasy) and DOM (STP).

"Heart valve disease" refers to distinctive valvular abnormality caused by a thickening of the leaflet and chordae tendineae. When one or more heart valves become diseased or damaged this affects the way that blood flows through the heart. This causes extra strain on the heart and causes symptoms such as chest pain, difficulty breathing and tiredness.

DETAILED DESCRIPTION

Preparation of Highly Purified CBD Extract

The following describes the production of the highly-purified (>98% w/w) cannabidiol extract which has a known and constant composition was used in the Examples below.

In summary the drug substance used is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 98% CBD. Although the CBD is highly purified because it is produced from a cannabis plant rather than synthetically there is a small amount of other cannabinoids which are co-produced and co-extracted with the CBD. Details of these cannabinoids and the quantities in which they are present in the medication are as follows:

| Cannabinoid | Concentration |
|---|---|
| CBDA | NMT 0.15% w/w |
| CBDV | NMT 1.0% w/w |
| $\Delta^9$ THC | NMT 0.15% w/w |
| CBD-C4 | NMT 0.5% w/w |

NMT—not more than

Example 1: Function of CBD & 7-OH-CBD at the Human $5\text{-HT}_{2B}$ Receptor Evaluation of the activity of CBD and 7-OH-CBD at the human $5\text{-HT}_{2B}$ receptor was undertaken in transfected CHO cells. Such activity as either an agonist or antagonist was determined by measuring their effects IP1 production using the HTRF detection method.

Materials and Methods

Antagonist Effects:

Cells were suspended in a buffer containing 10 mM Hepes/NaOH (pH 7.4), 4.2 mM KCl, 146 mM NaCl, 1 mM CaCl2, 0.5 mM MgCl2, 5.5 mM glucose and 50 mM LiCl, then distributed in microplates at a density of 4.104 cells/well and preincubated for 5 min at room temperature in the presence of buffer (basal control), test compound or reference antagonist.

Thereafter, the reference agonist 5-HT is added at a final concentration of 30 nM. For basal control measurements, separate assay wells do not contain 5-HT. Following 30 min incubation at 37° C., the cells are lysed and the fluorescence acceptor (D2-labeled IP1) and fluorescence donor (anti-IP1 antibody labelled with europium cryptate) are added.

After 60 min at room temperature, the fluorescence transfer is measured at ex=337 nm and λ em=620 and λ 665 nm using a microplate reader (Rubystar, BMG).

The IP1 concentration is determined by dividing the signal measured at 665 nm by that measured at 620 nm (ratio).

The results are expressed as a percent inhibition of the control response to 30 nM 5-HT. The standard reference antagonist is SB 206553, which is tested in each experiment at several concentrations to generate a concentration-response curve from which its IC50 value is calculated.

Agonist Effects:

Cells were suspended in a buffer containing 10 mM Hepes/NaOH (pH 7.4), 4.2 mM KCl, 146 mM NaCl, 1 mM CaCl2), 0.5 mM MgCl2, 5.5 mM glucose and 50 mM LiCl, then distributed in microplates at a density of 4.104 cells/well and incubated for 30 min at 37° C. in the presence of buffer (basal control), test compound or reference agonist.

For stimulated control measurement, separate assay wells contain 1 μM 5-HT. Following incubation, the cells are lysed and the fluorescence acceptor (D2-labeled IP1) and fluorescence donor (anti-IP1 antibody labelled with europium cryptate) are added.

After 60 min at room temperature, the fluorescence transfer is measured at A ex=337 nm and A em=620 and 665 nm using a microplate reader (Rubystar, BMG).

The IP1 concentration is determined by dividing the signal measured at 665 nm by that measured at 620 nm (ratio).

The results are expressed as a percent of the control response to 1 μM 5-HT. The standard reference agonist is 5-HT, which is tested in each experiment at several concentrations to generate a concentration-response curve from which its EC50 value is calculated.

Results

FIG. 1 describes the data produced by both the antagonist and agonist assays.

CBD and 7-OH-CBD were found to have Kb values of 3.7 (FIG. 1A) and 0.69 μM (FIG. 1B) respectively for the $5\text{-HT}_{2B}$ receptor. The Kb value represents the molar concentration of an antagonist (a drug that blocks a receptor target) required for 50% of the target protein (receptor) to have ligand bound to it at any one instant.

Neither CBD nor 7-OH-CBD possess agonist activity at $5\text{-HT}_{2B}$ receptors (FIGS. 1C and 1D).

Figure 2:
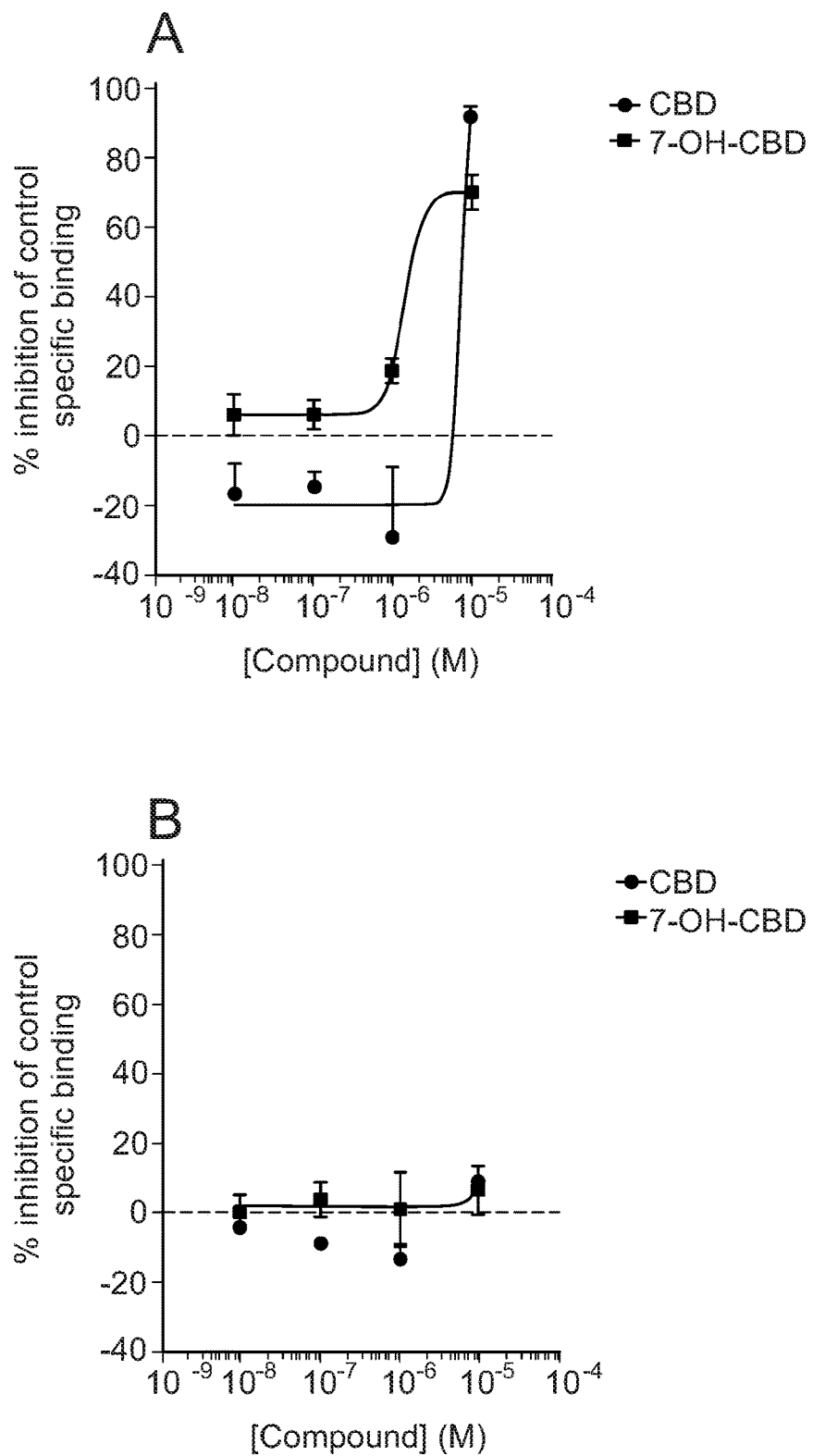
FIG. 2 shows the inhibition of specific binding at human recombinant 5-HT$_{2B}$ (A) and 5-HT$_{2C}$ (B) receptors by CBD and 7-OH-CBD.

Neither compound interacted with the $5\text{-HT}_{2C}$ receptor (as is shown in FIG. 2B).

Conclusions

In human clinical trials in epilepsy, CBD concentrations of up to 330 ng/mL have been reached in plasma which equates to a molar concentration of ~1 μM. Clinical use of CBD leads to the production of 7-OH-CBD which reaches concentrations of ~50% those achieved by CBD (i.e. ~0.5 μM).

Taken together, these affinity binding and clinical exposure data demonstrate that clinical use of CBD will produce sufficient CBD and 7-OH-CBD to engage and act upon the $5\text{-HT}_{2B}$ receptor.

The drug (+/−)-fenfluramine, and its human metabolites, (+/−)-nor-fenfluramine, bind to and activate a number of different human 5HT2 receptor subtypes (Rothman et al., 2000), including $5\text{-HT}_{2A}$, $5\text{-HT}_{2B}$ and $5\text{-HT}_{2C}$ at clinically relevant exposures. The interaction of these compounds with the $5\text{-HT}_{2B}$ receptor causes cardiovascular side effects (valvular heart disease) which were seen in clinical use of fenfluramine and was the reason it was withdrawn from its originally licensed clinical use for weight loss (Rothman and Baumann, 2009).

Fenfluramine is currently under investigation as a treatment for rare epilepsies (Dravet Syndrome and Lennox-Gastaut Syndrome). CBD also exerts beneficial therapeutic effects in these same epilepsies. There is evidence that fenfluramine's efficacy in epilepsy arises from its interaction with the $5\text{-HT}_{2C}$ receptor (Sourbron et al., 2016). However, some cardiovascular adverse effects have been reported in epilepsy patients treated with fenfluramine. Furthermore, the risk of developing cardiovascular side effects associated with fenfluramine use increase with both dose and duration of treatment (Schoonjans et al., 2017). Patients with the epilepsies described above develop their first symptoms in the early years of childhood and require lifelong drug treatment.

The co-administration of CBD with an agonist of the 5-$HT_{2B}$ receptors, such as fenfluramine, would reduce or prevent the valvular heart disease risk that is associated with agonism of the 5-$HT_{2B}$ receptors. This is due to the ability of CBD to block the 5-$HT_{2B}$ receptors preventing agonists such as fenfluramine from activating the receptors.

Furthermore, co-administration of CBD with pharmaceutical agents such as fenfluramine would not adversely affect its beneficial effects on therapeutic targets such as seizures as we show that CBD does not act upon the 5-$HT_{2C}$ receptors through which fenfluramine is proposed to exert its effects on seizures.

Example 2: Combination of Cannabidiol with Fenfluramine Produces Synergistic Reduction in Seizures The following example describes data produced from a combination of the cannabinoid CBD with the amphetamine derivative fenfluramine in a mouse model of seizure. Isobolographic analysis was undertaken to determine whether such a combination could produce a synergistic reduction in seizures.

Materials and Methods

The study was performed in two phases. Firstly, (Experiment A), a dose-dependent anticonvulsant effect of purified botanical CBD and fenfluramine (FEN) alone was demonstrated. Secondly, (Experiment B), drug-drug interactions (DDI) and anticonvulsant activities for CBD/FEN in combination were determined.

Experiment A was performed using 160 male, C57Bl6 mice, weighing between 20.1-30.1 g, and Experiment B was performed using 126 male, C57Bl6 mice, weighing between 19.2-26.1 g, purchased from a licensed breeder (Charles River, UK). There were no significant differences in animal weight among groups or between exhibits.

Naïve mice were acclimatised to the procedure room in their home cages, with food and water available ad libitum. Animals were housed in groups of 2-5, in standard caging on a 12 hr/12 hr light-dark cycle. All animals were tail marked, weighed and randomly assigned to vehicle or treatment groups at the beginning of the studies.

Anti-Epileptic Drugs (AEDS)

The following drugs were used in this study: Purified botanical CBD provided by GW Research Ltd., fenfluramine hydrochloride (FEN) purchased from Sigma Merck. The control vehicle used was 1:1:18 (5% ethanol, 5% Kolliphor EL, 90% saline). CBD and FEN were dissolved in the same control vehicle for comparison.

Animals were dosed (10 ml/kg) i.p. at 60 min for CBD and 30 min for FENS pre-treatment times, prior to MES and before plasma and brain sampling immediately post-MES test.

For Experiment A, in addition to the vehicle group, five dose groups were used for each active treatment. Here, doses were selected based on known ED50 and NOAELs for all the drugs and were: CBD-BOT [10, 30, 50, 70 and 100 mg/kg] and FEN [1, 2, 3, 5 and 10 mg/kg]. The number of animals in each of these groups were 10 (n=10), and 160 in total.

For Experiment B, in addition to the vehicle group, three dose groups were used for each of the treatments. Here, doses were selected based on analysis of the data obtained from Experiment A according to methods described for determination of isobolographic interactions. Doses as CBD/FEN combination were [20.9/2.5, 13.6/3.9 and 28.3/1.2 mg/kg]. The number of animals in each of these groups were 10 (n=10), and with individual CBD, FEN and VPA doses n=190 in total.

Maximal Electroshock Seizure (MES) Test

Electroconvulsions were produced by application of a fixed current intensity of 30 mA (0.2 sec duration) delivered via corneal electrodes. These parameters were previously validated to reliably produce tonic hind limb extension seizures in 100% of control animals. Mice were individually assessed for production of seizure determined by presence or absence of tonic hindlimb extension following current application.

Data were collected by an observer unaware of the treatment received by each animal. Data were expressed as the total number of animals exhibiting and not exhibiting hindlimb extension from which percentage inhibition of seizure vs the relevant vehicle group was derived.

Isobolographic Analysis of DDI

Isobolographic analysis is considered the gold standard for evaluating DDI; determination of equieffective doses of AEDs and the classification of DDI as synergistic (supra-additive), additive or antagonistic (sub-additive) in preclinical studies. Isobolograms are determined for both desired and adverse effects of the DDI ideally to find combinations that are synergistic for the desired effect and antagonistic for the adverse effect.

The protective activities of CBD and FEN administered alone were evaluated and expressed as effective doses ($ED_{50}$; mg/kg based on dose administered) and effective exposures ($EE_{50}$; µM based on bioanalysis of brain samples) where $EX_{50}$ is defined as the dose or brain exposure required to protect 50% of mice from MES-induced tonic seizures. CBD/FEN combinations were evaluated at 3 fixed ratios (1:3, 1:1 and 3:1) based on an $EE_{50}$ derived from an assumption of linearly additive effects of EEs of the two drugs in combination.

For the three fixed-ratio CBD/FEN combinations (1:3, 1:1 and 3:1), calculations were based on Loewe's equation of additivity as follows; $x/EE_{50}(CBD)+y/EE_{50}(FEN)=1$; where x=the exposure of CBD and y=the exposure at which CBD, when co-administered with FEN, should theoretically exert the desired/additive 50% effect. Subsequently, CBD and FEN doses corresponding to 50% of respective $EE_{50}$ were used for the CBD/FEN 1:1 ratio. Similarly, dose proportions were calculated for the CBD/FEN 1:3 and 3:1 ratios based on theoretical additive $EE_{50}$.

Statistical Analysis

All statistical tests were performed using GraphPad Prism v7.0 (GraphPad Software, San Diego, Calif., USA). Any differences between individual treatment groups and vehicle-treated controls were assessed using 2-tailed Fisher's Exact Probability Test ($p<0.05$ considered significant).

The percentage protection of animals against MES-induced seizure were plotted against doses of AED alone (CBD or FEN) from Experiment A as log-probit linear regression analysis to derive ED50 and EE50. For log-probit analysis, it is standard practice to select 4 doses that exhibit effects between 16% to 84% to determine effective doses for subsequent isobolographic analysis.

Loewe's equation of additivity was used to determine fractions of $EE_{50}$ in the three ratios 1:3, 1:1 and 3:1 for each of the combinations CBD/FEN. Graphs were plotted in Prism, for CBD and FEN to determine relationships versus these exposures to determine actual doses for the combination study (Experiment B).

DDI using these three-fixed dose-ratios of CBD/FEN was assessed using CalcuSyn v2.11 (Biosoft). Calcusyn determines the median-effect potency of drug alone ($D_m$) that inhibits the system by 50% and the coefficient m signifies the shape of the dose-effect relationship, where m=1, >1 and <1 indicate hyperbolic, sigmoidal and flat sigmoidal dose-effect curves. The combination index (CI) equation below quantitatively defines DDI as synergy (CI<1), additivity (CI=1) or antagonism (CI>1)

$$CI = \frac{(D)_1}{(D_x)_1} + \frac{(D)_2}{(D_x)_2} = \frac{(D)_1}{(D_m)_1[f_a/(1-f_a)]^{1/m_1}} + \frac{(D)_2}{(D_m)_2[f_a/(1-f_a)]^{1/m_2}}$$

where D1 and D2 are doses of drugs 1 and 2, fa is the fraction affected by D (percent inhibition/100), Dm is the median-effect dose and Dx is the dose required to inhibit the system by x %. Additionally, CalcuSyn was also used to generate normalised isobolograms for non-constant dose-ratio DDI and dose reduction index (DRI) for specific effects. DRI expresses dose reduction by folds of each drug in a synergistic combination at a given effect level compared to single administration.

Results

Experiment A:

Percentage Inhibition of Electroconvulsant Activity by Single AED

Figure 3:
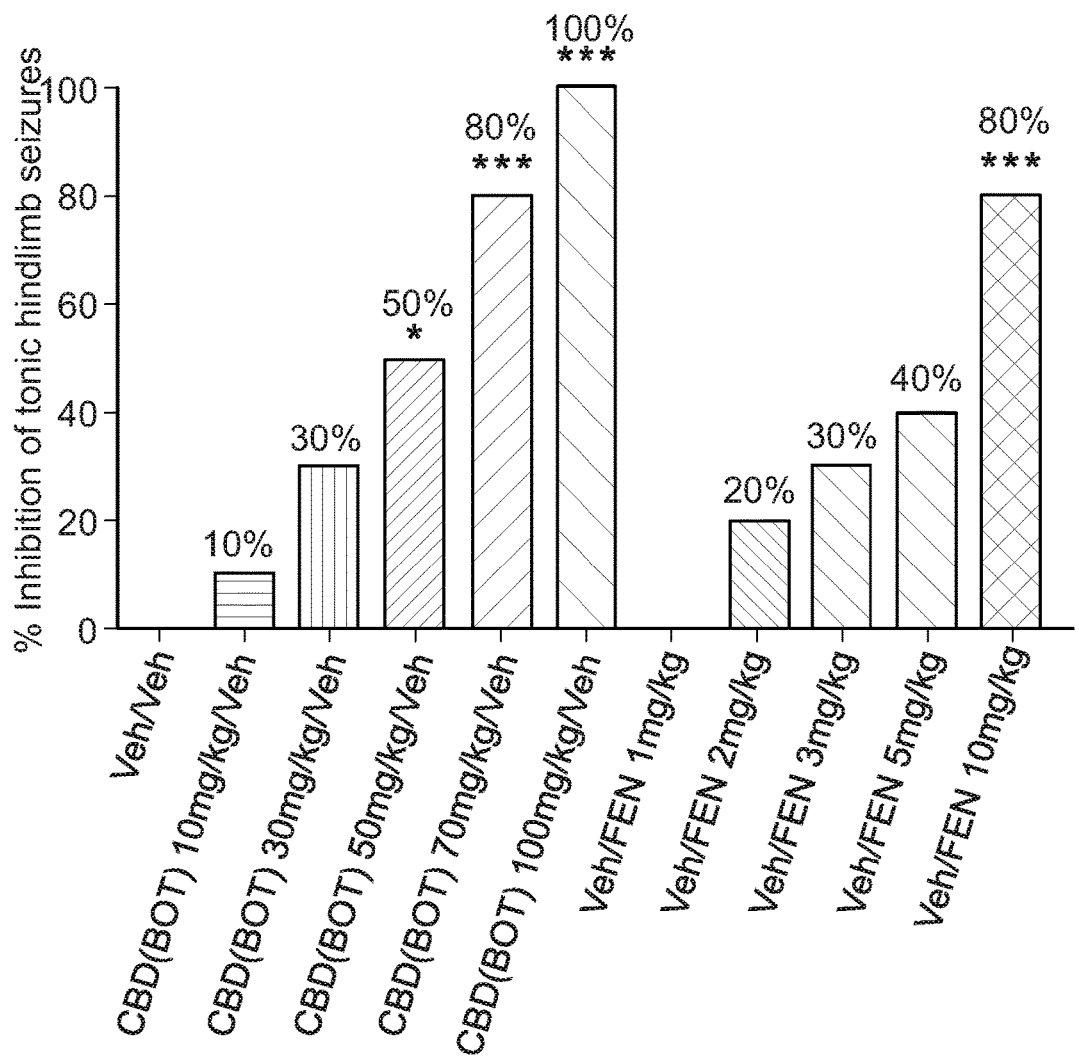
FIG. 3 shows the dose-dependent effects of CBD and FEN using mouse MES.

CBD and FEN both showed dose-dependent anticonvulsant effects on the incidence of maximal electroshock seizures when compared to vehicle. The per protocol analysis revealed statistically significant (p<0.05) anticonvulsant effects from 50-100 mg/kg for CBD and 10 mg/kg for FEN (FIG. 3).

CBD/FEN and CBD/VPA Dose Selection for Isobolographic Analysis

Based on the $EE_{50}$ values derived for CBD and FEN, the three fixed ratios (1:3, 1:1 and 3:1) were calculated using Loewe's equation of additivity (CBD/FEN: 1.6/29.7, 3.2/19.8 and 4.8/9.9 µM). Plots of doses versus average brain exposures were used to calculate CBD/FEN doses for the isobolographic analysis using linear equations. The CBD/FEN ratio-doses were 20.9/2.5, 13.6/3.9 and 28.3/1.2 mg/kg.

Experiment B:

Percent Inhibition of Electroconvulsions by CBD/FEN Combination

CBD or FEN alone exerted no significant effect on the incidence of maximal electroshock seizures (MES) when compared to vehicle at any of the doses tested, which was consistent to the low dose effects in the previous study (Experiment A).

Figure 4:
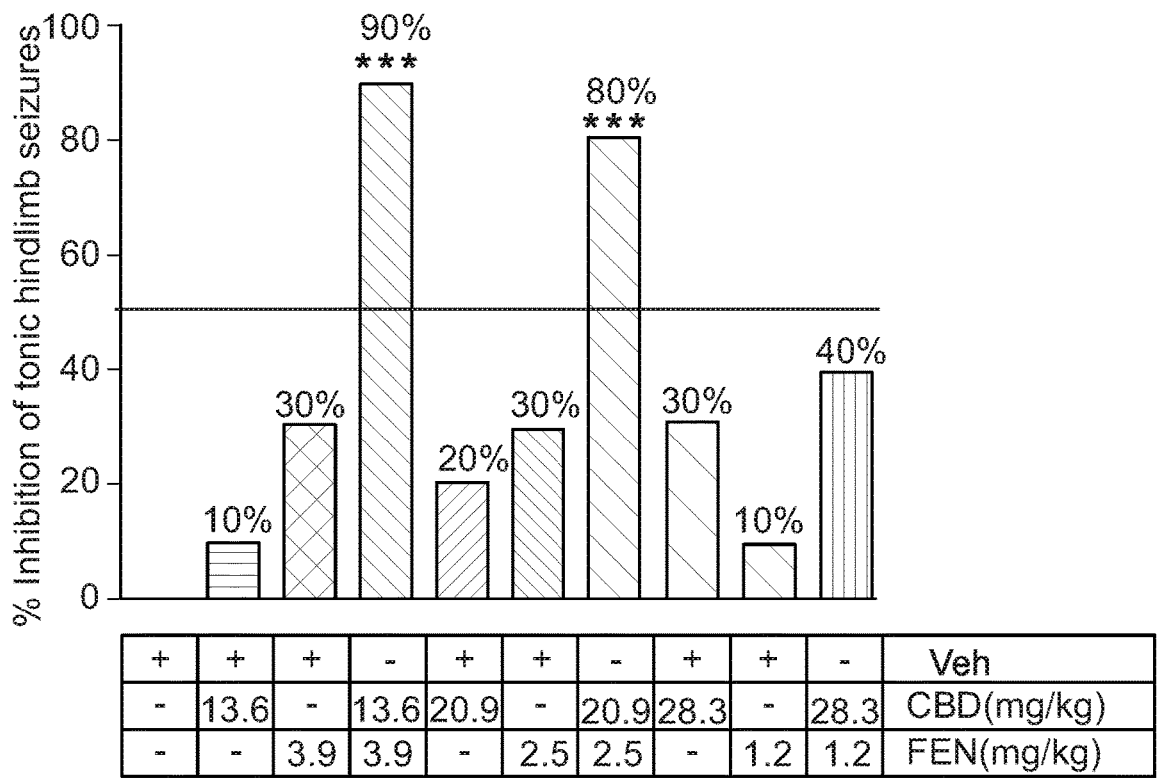
FIG. 4 shows the anticonvulsant efficacies of CBD/FEN ratio-dose combinations in the mouse MES.

In contrast, CBD plus FEN (p<0.01) produced significant anticonvulsant effects when compared with vehicle at two (CBD/FEN) of the ratio-dose combinations tested (FIG. 4).

Isobolographic Analysis of DDI Based Upon CBD/FEN Doses

The three fixed ratios of CBD/FEN 1:3, 1:1 and 3:1 corresponded to theoretically additive $EE_{50}$ values which, when adjusted to dose reflect ratios of 1:2.3 ($ED_{55}$+ADD), 1:1 ($ED_{50}$+ADD), and 3:1 ($ED_{46}$+ADD). As such, there is sufficient difference between dose and exposure ratios to reveal distinct effects.

Figure 5:
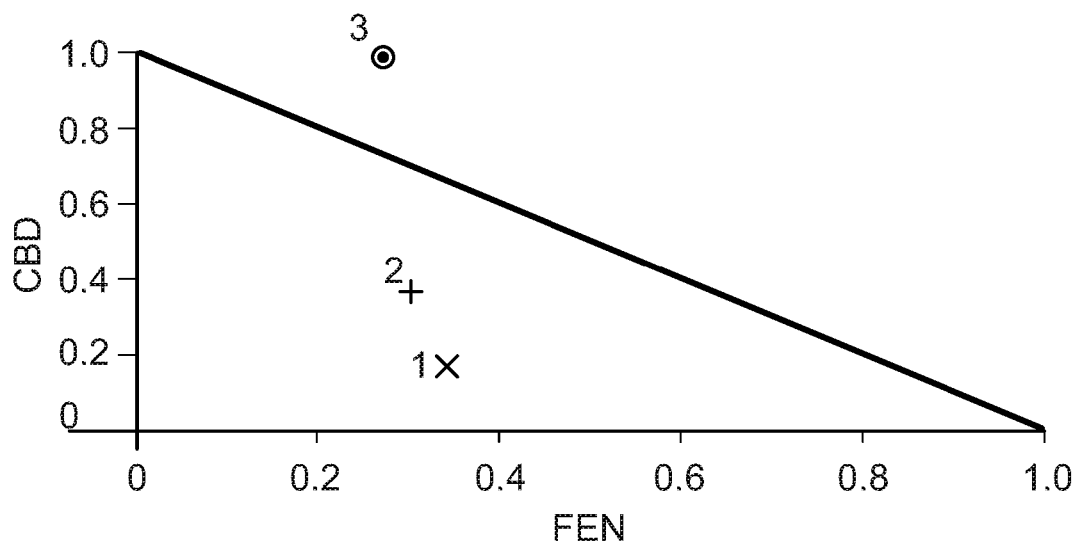
FIG. 5 shows the dose-normalised isobologram of CBD/FEN for non-constant ratio combinations in the mouse MES.

Median-effect curves for CBD and FEN doses derived potencies ($D_m$ or $ED_{50}$) of 33.2 mg/kg and 4.9 mg/kg. Simultaneously, m values of the dose-effect curves for CBD and FEN were also derived and found to be 2.6+0.5 and 2.6+0.7, where m>1 denotes a sigmoidal dose-effect relationship. The dose-normalised isobologram (FIG. 5) and CI (Table 5) revealed synergy for CBD/FEN at ratios of 1:2 and 1:1.

TABLE 5

Combination Index (CI) values for CBD/FEN doses

| CBD (mg/kg) | FEN (mg/kg) | CBD/FEN Ratio (theoretical ED) | Effect | CI | Description |
|---|---|---|---|---|---|
| 13.56 | 3.85 | 1:2 ($ED_{55+ADD}$) | 90% | 0.518 | Synergism |
| 20.91 | 2.5 | 1:1 ($ED_{50+ADD}$) | 80% | 0.672 | Synergism |
| 28.28 | 1.15 | 3:1 ($ED_{46+ADD}$) | 40% | 1.268 | Moderate antagonism |

Dose reduction index (DRI) calculations reports dose reduction of CBD by 5.690-fold and FEN by 2.921-fold when given in combination for a 90% anticonvulsant effect compared to administering either drug alone (Table 6).

TABLE 6

Dose Reduction index (DRI) values for CBD/FEN

| | Drug alone | | Dose Reduction Index (DRI) | |
|---|---|---|---|---|
| Effect | CBD (mg/kg) | FEN (mg/kg) | CBD (fold) | FEN (fold) |
| 90% | 77.15 | 11.24 | 5.690 | 2.921 |
| 80% | 56.55 | 8.26 | 2.704 | 3.306 |
| 40% | 28.46 | 4.19 | 1.006 | 3.639 |

Conclusions

These data indicate that the combination of CBD with fenfluramine at various ratios produced a synergistic reduction in seizures and as such could be a useful treatment option in difficult to treat childhood epilepsy syndromes such as Dravet syndrome or Lennox-Gastaut syndrome.

The maximal electroshock seizure (MES) test is widely used to evaluate anticonvulsant efficacies of standard antiepileptic drugs (AED). CBD and FEN showed dose dependent anticonvulsant effects on MES when administered alone, where significant (p<0.05) decreases in seizure incidence versus vehicle were observed at 50-100 mg/kg for CBD and 10 mg/kg for FEN.

CBD/FEN DDI were analysed based on dose-response and brain exposure-response effects using three combination doses of CBD/AED. Based on Loewe's equation of additivity, these correspond to CBD/AED ratios of 1:3, 1:1 and 3:1. The CI theorem and isobolographic analysis revealed CBD/FEN PD synergism at the 1:3 and 1:1 ratio.

OVERALL CONCLUSION

Taken together, the data from Example 1, which shows that CBD is able to prevent the valvopathy side effects produced by the 5-$HT_{2B}$ receptor agonists, and the data in Example 2 which demonstrates that a combination of CBD and the 5-$HT_{2B}$ receptor agonist and amphetamine derivative fenfluramine provides a synergistic reduction of seizures clearly demonstrates the highly therapeutic value of such a combination.

Furthermore, such a combination would enable a dose reduction of either the CBD or the 5-$HT_2B$ receptor agonist, amphetamine or amphetamine derivative. Given the known and harmful side effects demonstrated by 5-$HT_{2B}$ receptor agonist, amphetamine or amphetamine derivatives such as fenfluramine reducing the therapeutic dose of this class of compounds would be of great significance.

The invention claimed is:

1. A method of treating epilepsy comprising administering cannabidiol (CBD) in combination with fenfluramine; wherein the CBD: fenfluramine ratio ranges from about 1:1 to about 20:1 by weight.

2. The method of claim 1, wherein the combination of CBD and fenfluramine prevents or reduces one or more side effects associated with agonism of a $5\text{-HT}_{2B}$ receptor.

3. The method of claim 2, wherein the side effect that is prevented or reduced is heart valve disease.

4. The method of claim 1, wherein the CBD is in the form of a highly purified extract of cannabis which comprises at least 98% (w/w) CBD.

5. The method of claim 1, wherein the CBD is present as a synthetic compound.

6. The method of claim 1, wherein the epilepsy is treatment resistant epilepsy (TRE).

7. The method of claim 1, wherein the epilepsy is one of: Dravet Syndrome; Myoclonic-Absence Epilepsy; Lennox-Gastaut syndrome; Generalized Epilepsy of unknown origin; CDKL5 mutation; Aicardi syndrome; tuberous sclerosis complex; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome.

8. The method of claim 4, wherein the highly purified extract comprises less than 0.15% (w/w) THC.

9. The method of claim 4, wherein the highly purified extract comprises up to 1% (w/w) CBDV.

10. The method of claim 1, wherein the ratio of CBD to fenfluramine is between 10:1 to 1:1 by weight.

11. The method of claim 1, wherein the ratio of CBD to fenfluramine ranges from 3:1 to 1:1 by weight.

12. The method of claim 1, wherein the ratio of CBD to fenfluramine ranges from 2:1 to 1:1 by weight.

13. The method of claim 1, wherein the ratio of CBD to fenfluramine is approximately 1:1 by weight.

14. The method of claim 1, wherein the dose of CBD is between 5 mg/kg/day and 50 mg/kg/day.

15. The method of claim 1, wherein the dose of fenfluramine in a mouse is at least 1.2 mg/kg.

16. The method of claim 1, wherein the dose of fenfluramine in a mouse ranges from 1.2 mg/kg to 3.9 mg/kg.

17. The method of claim 7, wherein the epilepsy is treatment resistant epilepsy (TRE).

* * * * *